United States Patent [19]

Houswerth

[11] Patent Number: 4,620,532

[45] Date of Patent: Nov. 4, 1986

[54] ADJUSTMENT DEVICE FOR AN ARTICULATED JOINT BRACE

[75] Inventor: John R. Houswerth, Bourbonnais, Ill.

[73] Assignee: Lenox Hill Brace Shop, Inc., New York, N.Y.

[21] Appl. No.: 536,083

[22] Filed: Sep. 26, 1983

[51] Int. Cl.[4] ............................ A61F 5/04; A61F 5/37
[52] U.S. Cl. ................... 128/80 C; 128/80 F; 128/88
[58] Field of Search ............... 128/80 C, 80 F, 80 R, 128/88; 3/22, 1.911, 26, 12.2; 403/116, 117

[56] References Cited

U.S. PATENT DOCUMENTS

| | | | |
|---|---|---|---|
| 2,557,604 | 11/1949 | Invidiato | 128/80 F |
| 4,340,041 | 7/1982 | Frank | 128/80 C |
| 4,353,361 | 10/1982 | Foster | 128/80 C |
| 4,370,977 | 2/1983 | Mauldin et al. | 128/88 |
| 4,463,751 | 8/1984 | Bledsoe | 128/80 C |
| 4,481,941 | 11/1984 | Rolfes | 128/88 |
| 4,520,804 | 1/1985 | DiGeorge | 128/80 C |

*Primary Examiner*—Edgar S. Burr
*Assistant Examiner*—Tonya Eckstine
*Attorney, Agent, or Firm*—Blum Kaplan Friedman Silberman & Beran

[57] ABSTRACT

Two substantially planar discs sandwich pivoting joint elements therebetween. Slides, also between the discs, can move independently in a wide range of angular positions about the pivoting axis of the joint, and be fixed in any selected positions. Slides comprise two elements drawn together radially to clamp onto circumferential rims provided on the discs. Joint bending in each direction is independently controlled. Internal opposed teeth on the disc rims and slides engage when the slides are positioned.

18 Claims, 7 Drawing Figures

FIG. 1
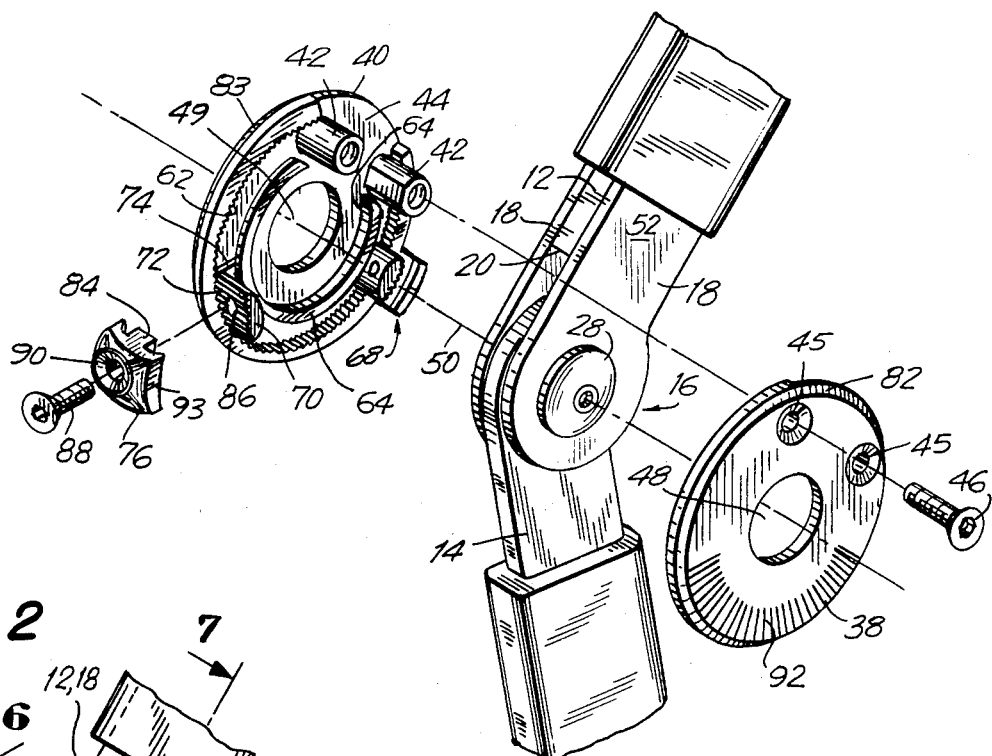
FIG. 2
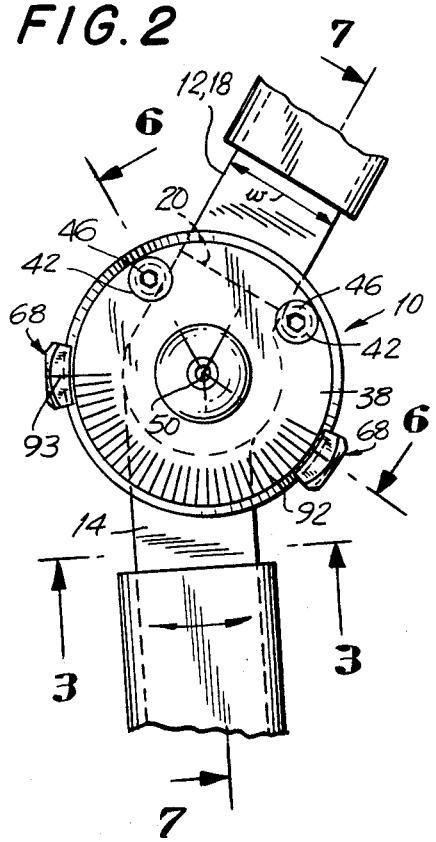
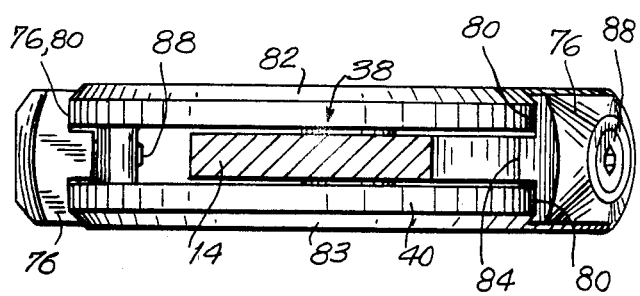
FIG. 3

ADJUSTMENT DEVICE FOR AN ARTICULATED JOINT BRACE

BACKGROUND OF THE INVENTION

This invention relates generally to a brace which is used at joints of the human body to reinforce and to prevent injury thereto by constraining the motion of articulated members and more particularly to an adjustment device which sets limits to the relative motion of the articulated members at the joint. Such a brace is used particularly under conditions where the portion of the body to which the brace is applied is prone to injury or must be protected after surgery following an injury. When a joint is reinforced during post-operative periods where joint bending is desirably restrained, means must be provided to set the rigid members of the brace at a selected angle during the healing period. As the joint heals, the angle setting between the members is changed allowing additional bending at the joint. In reinforcing, for example, a knee joint, a brace as disclosed in U.S. Pat. No. 3,669,105, issued June 13, 1972, is used. As stated, it is desirable to allow for a degree of bending at the joint during the healing process after surgery. The amount of bending is progressively increased as the joint becomes stronger.

After the joint is healed, the need for adjustability in the bending angle permitted at the joint may no longer exist and a single setting of a maximum permissible bending angle may be provided. On the other hand, the recovered joint may function without any artificial restraints to bending at the joint, while reinforcement against bending along undesirable axes is still necessary and provided by retention of the joint brace. Unfortunately, in the prior art, the devices and mechanisms for limiting the amount of bending at a joint which is reinforced by a brace, are permanent features of the brace. Thus unnecessary structure, interfering with clothing, adding weight, and adversely affecting the convenience in using the leg brace remains after the need for adjustment is past. To eliminate these unnecessary elements, a new brace or new components for the brace are required, thus incurring additional expense and need for assembly and disassembly which frequently can not be accomplished except by those knowledgeable of the brace construction and having access to special tools.

Additionally, a need for a brace to restrict bending may develop for a user of a brace currently permitting a wide range of bending. In the past it would be necessary to procure a new brace or costly, frequently customized modification would be required to adapt the original brace to the new requirements.

What is needed is an adjustment device for limiting motion of an articulated joint brace which is readily attached and removeable from the brace without special tooling, and without modification to existing brace members, and which allows for adjustment in two directions in the degree of bending at the reinforced joint within desired limits.

SUMMARY OF THE INVENTION

Generally, in accordance with the invention, an adjustment device for an articulated joint brace especially suitable to restrain bending at the joint within prescribed limits is provided. The adjustment device attaches to an existing leg brace without alteration or modification to the leg brace itself. It is easily added and adjusted by the user as required. The adjustment device clamps over the joint where two brace members are pivotably joined together, and is centered around the pivoting axis of the joint by means of a central hole in the adjustment device.

The adjustment device comprises two substantially planar discs which sandwich the pivoting joint elements therebetween. Slides, also sandwiched between the discs, can be moved in a wide range of angular positions about the pivoting axis of the joint, and fixed in any selected positions. The slides comprise two elements which are drawn together radially by set screws to clamp onto circumferential rims provided on the discs. The position of each slide is independently adjustable such that joint bending in each direction can be independently controlled. Internal teeth are provided on the circumferential disc rims and the slides are formed with opposing teeth which engage the circumferential rims when the slides are firmly positioned by means of the set screws.

Accordingly, it is an object of this invention to provide an improved adjustment device for an articulated joint brace which controls the amount of flexion and extension movement of a pair of joined limbs, one with respect to the other about a single desirable axis.

Another object of this invention is to provide an improved adjustment device for a joint brace for articulated limbs which can be added and removed from a conventional brace without modification to the brace.

A further object of this invention is to provide an improved adjustment device for a joint brace for articulated limbs which is comprised of a relatively small number of simple, lightweight components which are easily applied to a conventional leg brace and easily adjusted for the desired degree of joint bending by the user.

Still another object of this invention is to provide an improved adjustment device for a joint brace for articulated limbs which positively holds angular settings limiting the amount of bending at a supported joint.

Still other objects and advantages of this invention will in part be obvious and will in part be apparent from the specification.

The invention accordingly comprises the features of construction, the combination of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is an exploded perspective view of the adjustment device for an articulated joint brace in accordance with the invention in relation to the pivoting joint of an articulated limb brace;

FIG. 2 is a side elevational view of the adjustment device for an articulated joint brace of FIG. 1, shown connected to a limb brace;

FIG. 3 is a side elevational view to an enlarged scale taken along the line 3—3 of FIG. 2;

DESCRIPTION OF THE PREFERRED EMBODIMENTS

Braces are commonly used to support weak or injured joints between articulated body members, for example, at the knee joint which connects the upper and lower limbs for pivoting motion with respect to each other about a particular axis. Most articulated limb braces provide rigid members, which are attached respectively to the articulated limb members and pivoted about an axis which is co-linear with the bending axis of the limb joint. Pairs of joined, pivoted brace members may be attached on opposite sides of the limb joint, for example, in supporting a knee joint as illustrated in U.S. Pat. No. 4,340,041. On the other hand, in the U.S. Pat. No. 3,669,105, cited above, brace members on only one side of the joint are pivotably connected about an axis colinear with the axis of the joint. It should be understood that the adjustment device for an articulated joint brace in accordance with the invention is applicable to limit the pivoting motion of the brace whether leg brace provides a pivotably joined rigid members on one or both sides of the reinforced body joint.

Figure 7:
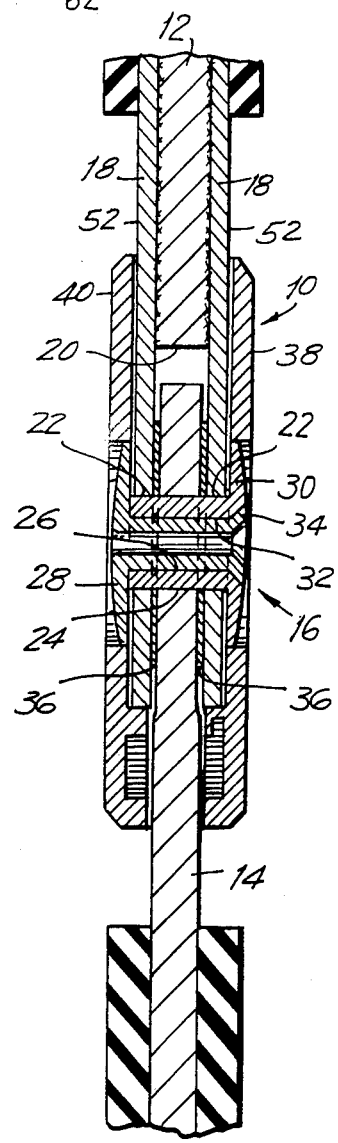
FIG. 7 is a sectional view to an enlarged scale taken along the line 7—7 of FIG. 2.

The adjustment device 10 for an articulated joint brace in accordance with the invention is now described for application to a pivotable joint in a leg brace, the leg brace joint construction being best illustrated in FIGS. 1 and 7. The leg brace includes an upper arm 12 and a lower arm 14 which are pivotably joined together at a joint 16. The joint 16 includes a pair of plates 18, fixedly attached to the opposed side planar surfaces of the upper arm 12 so as to partially overlap and partially extend beyond the end surface 20 of the arm 12. The plates 18 are connected to the arm in any suitable manner, for example, welding, riveting, so as to provide substantially planar exterior surfaces for the plates 18. Holes 22 are located coaxially on the opposed plates 18 and when the lower arm 14 is inserted between the plates 18, a hole 24 through the arm 14 aligns with the holes 22 such that a hollow pin 26, connected to a larger diameter head disc 28, is inserted through the aligned holes 22, 24 to engage a washer 30 having a hole 32 through which the pin 26 passes. As best seen in FIG. 7, the pin 26 is swaged in the opening 34 of the washer 30 such that once assembled, the pin 26 is not readily withdrawn while the arms 12, 14 are joined together in a pivoting joint. Clearance is provided between the hole 32 and pin 26, and between the holes 22 in the plates 18 and washer 30, whereby the arms 12, 14 turn freely without binding about the pivot 26, 30. Washers 36 on both sides of the arm 14 and riding on the washer 30 eliminate frictional contact between the arm 14 and the inner surfaces of the plates 18.

In the construction as described above, the degree of pivoting motion about the joint 16 without an adjustment device 10 is limited only by mechanical interference between the end and side surfaces of the arm members 12, 14 and the plates 18. Pivoting motion is possible in either direction such that a narrow angle may be formed between the upper and lower arms 12, 14, although it should be understood, that in different embodiments, different coverings, paddings, and the like attached to the arm members 12, 14 may provide a limit to the maximum degree of bending which is possible.

FIG. 2 illustrates the adjustment device 10 for an articulated joint brace in accordance with the invention attached to the brace joint of FIG. 1. The adjustment device 10 for an articulated joint brace includes a face disc 38 and a back disc 40 opposed to each other and held apart by a pair of spacers 42 extending from an inner surface 44 of the back disc 40. Holes 45 in the face disc 38 are aligned to the spacers 42 and holding screws 46 pass through the holes 45 and engage internal threads in the hollow spacers 42 to hold the discs 38, 40 in a spaced but fixed relationship.

The connected discs 38, 40 have central openings 48, 49 in alignment. When the adjustment device 10 for an articulated joint brace in accordance with the invention is applied to the joint 16 of the leg brace of FIG. 1, the central openings 48, 49 receive the head disc 28 in one opening and the washer 30 in the opposite opening such that the adjustment device 10 for an articulated joint brace is positioned with the centers of the central openings 48, 49 substantially co-linear with the pivoting axis of 50 the brace joint 16. As best seen in FIG. 2, the upper arm 12 extends from the adjustment device 10 between the spacers 42. Therefore, potential motion of the upper arm 12 relative to the adjustment device 10 is limited by the spacing between the spacers 42 and the width w of the upper arm 12. As illustrated, the width w of the arm 12 and the distance between the spacers 22 allows little if any motion of the arm 12 relative to the adjustment device 10 about the pivoting axis 50 of the joint 16. As discussed more fully hereinafter, the face disc 38 and back disc 40 may or may not clamp against the flat planar surfaces 52, of the plates 18 on the upper arm 12.

Figure 4:
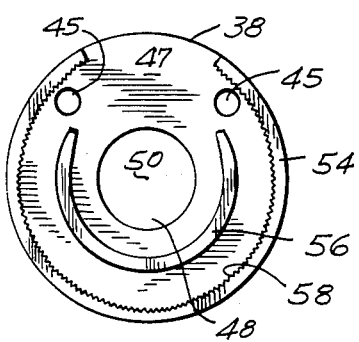
FIG. 4 is an inside view of a face disc of the adjustment device for an articulated joint brace of FIG. 1.

The face disc 38 includes a peripheral rim 54 extending from the inner surface 47, the rim 54 being interrupted generally in the vicinity of the holes 45 (FIG. 4). A second rim 56 extends from the surface 47 concentric with the peripheral rim 54, being somewhat more than a semi-circle and terminating proximate the holes 45. Teeth 58 extend transversely to the surface 44 on the inner surface of the peripheral rim 54.

The back disc 40 in addition to having the internally threaded spacers 42 extending from the planar internal surface 44, includes a peripheral rim 60 extending from the surface 44 and terminating promixate the spacers 42. Teeth 62 are formed on the inner surface of the peripheral rim 60 extending transversely from the surface 44. The teeth 58, 62 on both discs 38, 40 have the same pitch and profile and are angularly positioned relative to the center line axis 50 such that when the discs 38, 40 are mated for assembly as shown in FIGS. 1 and 2, the teeth 58, 62 are in alignment between the surfaces 44, 47.

A track 64 also extends from the surface 44 of the back disc 40. The track 64 is in the shape of an inverted L (FIG. 6) such that an undercut region 66 is provided between the surface 44 and the upper arm of the L-shaped track 64.

Figure 5:
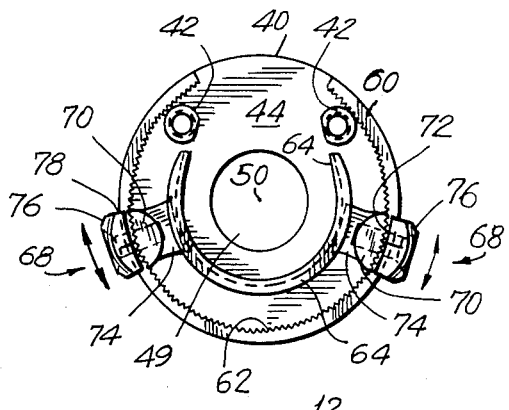
FIG. 5 is a view similar to FIG. 2 with the face disc and holding screws removed from the adjustment device for an articulated joint brace of FIG. 1.
Figure 6:
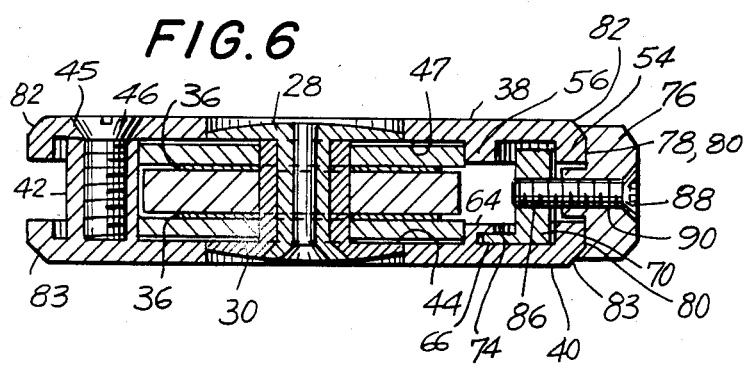
FIG. 6 is a sectional view to an enlarged scale taken along the line 6—6 of FIG. 2.

Slides 68 are comprised of three elements. The inner slide element 70 (FIG. 6) includes teeth 72 on a curved surface, the curvature thereof matching the curvature of the peripheral rims 54, 60 and the teeth having the same pitch and profile. The height of the inner slide element 70 allows for a sliding fit of the inner slide element between the surfaces 44, 47 when the face disc 38 and back disc 40 are joined together by means of the holding screws 46 (FIG. 6). As best seen in FIGS. 5 and 6, a web 74 extends from the inner slide element 70 resting on the surface 44 and engaging the under cut 66 produced by the track 64 with the back disc 40.

An outer slide element 76 includes a surface 78 which is curved to slide on the circumferential outer surfaces of the discs, 38, 40 and has undercuts 80 to receive the beveled edges 82, 83 on the disc 38 and back disc 40 respectively.

A protrusion 84 on the outer slide element 76 extends into the space between the rims 54, 60 and in conjunction with the undercuts 80 allows the outer slide elements 76 to ride on the outer circumferential surfaces of the face and back discs 38, 40 as on a two-rail track.

A threaded hole 86 in the inner slide element 70, receives a set screw 88 passing through a beveled clearance hole 90 in the outer slide element 76. When the set screw 88 is tightened, the inner slide element 70 and outer slide element 76 are radially drawn together until the teeth 72 on the inner slide element 70 engage with the teeth 58, 62 on the face and back disc peripheral rims 54, 60, whereby a positive connection is made between the slide 68 and the discs 38, 40.

The extent of the undercut 66 and the length of the web 74 on the inner slide elements 70 are such that when the set screw 88 is loosened, without separating the set screw 88 from the threads in the hole 86, the inner slide element 70 may be pushed radially inward by slight pressure on the set screw 90, causing the teeth 72 on the inner slide element to disengage from the teeth 58, 62 on the rims 54, 60 respectively. Thus the slide may be moved to any angular position around the pivot axis 50, each slide being limited in its motion, absent the brace arms 12, 14, only by the presence of the other slide and the spacers 42.

Application of the adjustment device 10 for an artificial joint brace to a brace and adjustment of the permissible pivoting motion about the joint axis 50 is now described. Assuming that the adjustment device 10 for an artificial joint brace is completely assembled but not applied to a leg brace, the first step in installation of the adjustment device 10 is removal of the holding screws 46 with an appropriate wrench or screw driver depending upon the head of the set screw 88 which is selected. A set screw 88 for operation with an Allen wrench is illustrated in the Figures only as an example. When the set screws 88 are loosened, the face disc 38 is separable from the remaining structure by a slight tilting action. As best seen in FIG. 5, the slides 68 can now be set to any angular position around the pivot axis 50. It should be noted that the webs 74 remain engaged in the undercut 66 of the track 64 except when the set screws 90 are substantially loosened or removed. Thus, when the face disc 38 is removed from the assembly of the adjustment device, no parts fall free and an adjustment device, packaged in an assembled condition, remains substanatilly as illustrated in FIGS. 1 and 5 when the face disc 38 is removed. Thus, even one possessing only minor mechanical skills is able to apply the adjustment device 10 to the joint of a brace without complete disassembly of the device, and without any disassembly of the brace. There is no need to handle a multitude of small, loose parts.

The brace is then cradled between the exposed spacers 42 and between the two loosened slides 68. The face disc 38 is put in position for engagement of the holding screws 46 with the threaded spacers 42 through the holes 45. While the spacers are loosely gripped by the screws 46, there is no problem in slipping the face disc 38 within the undercut 80 on the outer slide element 76.

The inner slide elements 70 are not yet in engagement with the teeth of the rims 54, 60. Then, the holding screws 46 are tightened while the protrusions 28, 30 on the brace enter the central openings 48, 49 on the discs 38, 40 to assure that the central axis of the adjustment device 10 is co-linear with the pivoting axis 50 of the joint in the leg brace for an articualted limb. Finally, the slides 68 are moved to their desired angular positions and tightened in place by tightening the set screws 88. Markings 92, 93 on the exterior of the face disc 38 and on the slide's outer element 76 allow for precise and repeatable setting and adjustment of position of the slides 68.

Obviously the slides may be tightened in position before the holding screws 46 are tightened. Also it should be noted that subsequent adjustment to the permitted range of joint pivoting is accomplished merely by loosening one or both slide set screws 88, as required. No disassembly is required.

As stated above, when the distance between the spacers 42 corresponds with the width w of the brace element, the brace arm 12, 18 located between the spacers 42 is not permitted to turn angularly with respect to the adjustment device 10. However, the lower arm 14 is free to turn about the pivot axis 50, being constrained in one direction by a slide 68 and in the other direction by the other slide 68. Obviously, if the slides 68 are brought closer together they may be made to clamp about the lower arm 14. In such an instance no pivoting will be permitted around the joint axis 50, however, many angles between the upper and lower arms 12, 14 can be selected for this fixed condition.

On the other hand, in an alternative brace construction the width w of the upper arm 12, 18 may be less than the spacing between the spacers 42. Then relative rotational motion is possible between the adjustment device 10 and the upper arm 12. Because the spacers 42 are fixed in position, this motion would represent a minimum amount of motion possible for the brace about the pivot axis 50 when the slides 68 are used to press on both sides of the lower arm 14. Additional angular motion is then permitted by setting the slides 68 away from the lower arm 14 to any selected positions. Thus, in the alternative brace construction, both arms 12, 14 are capable of pivoting relative to the adjustment device 10 as well as in relation to each other.

In another alternative embodiment of an adjustment device in accordance with the invention, the clearance between the rims 54, 60 on the discs 38, 40 respectively, is reduced proximate to the spacers 42 such that when the holding screws 46 are tightened the discs 38, 40 clamp onto the plates 18, connected to the upper arm 12, rigidly holding the upper arm 12 relative to the adjustment device 10.

Although, in the illustrated embodiment described above, the toothed rims 54, 60 and track 56 are circular, it should be understood that in alternative embodiments, these elements may have other contours, for example, parabolic, or include portions of different radii blended together in a continuous path, or the tracks and rims may be linear such that linear racks replaces the rims in the illustrated embodiment which are in the form of internal gears. In such an alternative embodiment, the mating surfaces on the slide 68 are linear. Operating principles are the same.

As best seen in FIG. 1, the face disk 38 serves as a supplement to the functions performed by the back disk 40. Also, the face disk provides a smooth exterior appearance to the device and also minimizes the risk of catching with clothing or scratching a person or object. In particular, the face disk 38 provides an additional rim 54 with teeth 58 which perform the same function as the rim 60 and teeth 62 of the back disk 40. Thus, in an alternative embodiment (not shown) of an adjustment device for articulated joint brace in accordance with the invention, the face disk 38 is omitted and is replaced by a small plate having clearance holes spaced apart by the distance between the spacers 45. In assembling the device to a brace joint, the device is centered on the joint by the opening 49 as described above, and held in place by the plate which is connected to the spacers 45 after the arm 12, 18, has been seated between the spacers 42.

In such an embodiment the rim 60 is extended for a greater distance from the planar surface 44 of the back disk 40 so as to provide adequate gripping surfaces for the slides 68. Markings, similar to the markings 92 may be placed on the surface 44 between the rim 60 and the track 64 or on the exposed edge of the rim 60. Proportions of the slides are modified to adapt to the greater depth of the teeth on the rim 60. The device functions as described above.

In another alternative embodiment (not shown) of an adjustment device in accordance with the invention, both the face disk 38 and also the spacers 42 are eliminated and replaced by a U bolt and nuts. The U bolt surrounds the arm member 12, 18 and threaded ends of the U bolt pass through holes in the back disk 40, the holes being located where the spacers 42 are positioned in the embodiments described above. Then, the nuts are attached to the threaded ends of the U bolt to clamp the adjustment device to the brace, positioning being achieved as before by the opening 49 engaging a protrusion 28 on the brace.

The teeth on the rims and slides provide a mechanical obstruction to any unintended change in position of the slides under loads produced by the user of the brace. Resistance of the teeth in shear opposes such forces, allowing parts to be fabricated of metal such as aluminum and steel, for examples, and high strength plastic, for example, polycarbonate. Castings and machined parts are suitable. The slide set screws 88, in their radial orientation, are not subjected to loads which are opposed by the teeth and therefore resist loosening in use.

It will thus be seen that the objects set forth above, and those made apparent from the preceding description, are efficiently attained and, since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. An adjustment device for a brace for an articulated limb, said brace including an upper arm and a lower arm, an end of each said arm being coupled together for pivoting about a joint axis, comprising:
a face member and a back member;
at least two spacers located between said face member and back member separating said members, the space between said members being sufficient to receive therein said arms at said joint axis;
means for holding said face and back members releasably together, separated by said at least two spacers;
means for positioning said face and back members relative to said pivoting joint axis of said brace when said members are held together by said means for holding, separated by said spacers, and have said arms at said joint axis in said space between said face and back members;
a rim extending respectively from at least one of said face and back members;
a pair of slides for releasably clamping said rim at selectable positions along said rim, the angle formed between said pair of slides and said pivoting axis being a variable dependent upon the selected positions for clamping said slides on said rim, and
interengagement means on said rim and said slides for mechanically preventing motion of said slides along said rim when said slides are clamped to said rim, said interengagement means including teeth formed on the mating surface between said rim and said slides, said teeth intermeshing when said slides are clamped to said rim, said teeth being subject to disengagement when said slides are not clamped on said rim.

2. An adjustment device as claimed in claim 1, wherein said means for positioning said face and back members relative to said pivoting joint axis include knob-like protrusions on said brace at said joint between said upper and lower arms, and openings in said face member and back member, said openings being contoured to receive said knob-like protrusions with a fit positioning said face and back members relative to said pivoting joint axis.

3. An adjustment device as claimed in claim 1, wherein said spacers are separated by a distance substantially equivalent to the width of one of said brace arms, said one brace arm extending from said adjustment device between said spacers when said face and back members are held by said means for positioning relative to said pivoting joint axis with said joint arms and said spacers between said face and back members, and wherein said slides are subject to positioning on said rim so as to allow the other brace arm to extend from said adjustment device between said slides, said arms being pivotable about said axis in a range determined by said angle between said axis and said slides.

4. An adjustment device as claimed in claim 3, wherein each of said face and back members include a rim, said rims extending toward each other and separated by a distance allowing a non-binding fit between both said upper and lower arms of said brace and said rims.

5. An adjustment device as claimed in claim 3, wherein the distance between said spacers allows no substantial motion relative to said spacers of said one brace arm passing therebetween.

6. Adjustment device as claimed in claim 5, wherein each of said face and back members includes a rim, said rims extending toward each other and separated by a distance allowing a non-binding fit between both said upper and lower arms and said rims.

7. An adjustment device as claimed in claim 5, wherein each of said face and back members includes a rim, said rims extending toward each other and separated by a distance permitting relative motion with respect to said rims of only said other one of said arms.

8. An adjustment device as claimed in claim 3, and further comprising a track positioned at a distance from said rim, and respective webs extending from each said slide, the web of each said slide being constrained by said track when said slide clamps said rim, said webs remaining constrained when said slides are released from said rim sufficiently to allow for selection of positions of said slides along said rim.

9. An adjustment device as claimed in claim 8, wherein said spacers are internally threaded and integral with said member having said track thereon, and said means for holding said face and back members releasably together includes a screw passing through a clearance hole in the other said member and engaging said threads in said spacers.

10. An adjustment device as claimed in claim 8, wherein said track provides an undercut said webs being cradled in said undercut when said slides are clamped to said rim.

11. An adjustment device as claimed in claim 8, wherein each of said face and back members has a generally planar surface, said at least two spacers separate said planar surfaces, said arms at said joint being received in the space between said planar surfaces.

12. An adjustment device as claimed in claim 11, wherein said rim extends from the planar surface of at least one of said face and back surfaces, said slides each defining a path along said rim, the paths of said slides along said rim being in a plane perpendicular to said joint pivoting axis, said slides being positioned between said planar surfaces.

13. An adjustment device as claimed in claim 12, wherein said interengagement means are teeth on the mating surfaces of said rim and said slides, said teeth extending transversely to said planar surfaces.

14. An adjustment device as claimed in claim 13, wherein a rim extends from each said planar surface, both said rims having said teeth and being portions of circles of equal diameter and concentric with said pivoting joint axis when said adjustment device is held by said means for positioning relative to said joint axis, and said track is located on one of said planar surfaces, said track being a portion of a circle concentric with and having a lesser diameter than the associated rim.

15. An adjustment device as claimed in claim 13, wherein said slide includes an outer slide element contoured to slide on the outside of said rims, and an inner slide element having said teeth for mating with said rim teeth, said rim teeth being located on the inner surfaces of said rims.

16. An adjustment device as claimed in claim 15, wherein said inner and outer slide members are joined together by a set screw passing through said outer slide member and engaging threads in said inner slide member, tightening said set screw clamping said slide to said rim.

17. An adjustment device for a brace for an articulated limb, said brace including an upper arm and a lower arm, an end of each said arm being connected together for pivoting about a joint axis, comprising:

a face member and a back member, each said member having a planar surface;

a pair of spacers located between said planar surfaces separating said face and back members by a fixed distance, the space between said members being sufficient to receive therein said arms at said joint axis;

means for holding said face and back members releasably together, separated by said spacers;

an individual rim extending from each of said planar surfaces, said rims extending toward each other, an open space being between said rims when said face and back members are held together separated by said spacers, said rims being portions of equal diameter circles and having teeth formed on the inner curved surfaces thereof, said teeth extending transversely to said planar surfaces;

means for positioning said face and back members relative to said pivoting joint axis of said brace when said members are held together by means for holding, separated by said spacers, and have said joined arms in said space between said face and back members, said face and back members being positioned such that said rim circles are concentric with said pivoting joint axis;

a pair of slides for releasabley clamping said rims at selectable positions along said rims, the angle formed between said slides and said pivoting axis being a variable dependent upon the selected positions for clamping said slides, each said slide includes an external slide element contoured to slide on the outside of said rims, and an internal slide element having teeth for mating with said teeth on said inner rim surfaces, said internal and external slide members being joined together by a set screw passing through said external slide member and engaging threads in said internal slide member, tightening said set screws clamping said slides to said rims with said teeth interlocked, a clamping force provided by said set screw acting radially to said rims, said set screw passing through said opening between said rims to join said internal and external slide members.

18. An adjustment device as claimed in claim 17, wherein said spacers are separated by a distance permitting one arm of said brace to extend from said adjustment device between said spacers when said face and back members are held by said means for positioning relative to said pivoting joint axis with said joint arms and said spacers between said face and back members, and said slides being subject to positioning on said rims so as to allow the other brace arm to extend from said adjustment device between said slides, said arms being pivotable about said axis in a range determinted by said angle between said axis and said slides.

* * * * *